United States Patent
Kondo et al.

(10) Patent No.: US 10,646,800 B2
(45) Date of Patent: May 12, 2020

(54) FILTRATION FILTER DEVICE

(71) Applicant: Murata Manufacturing Co., Ltd., Nagaokakyo-shi, Kyoto-fu (JP)

(72) Inventors: Takashi Kondo, Nagaokakyo (JP); Masaru Banju, Nagaokakyo (JP); Junko Watanabe, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 85 days.

(21) Appl. No.: 15/938,177

(22) Filed: Mar. 28, 2018

(65) Prior Publication Data
US 2018/0207555 A1    Jul. 26, 2018

Related U.S. Application Data

(63) Continuation of application No. PCT/JP2017/001590, filed on Jan. 18, 2017.

(30) Foreign Application Priority Data

Feb. 15, 2016 (JP) .................. 2016-025954

(51) Int. Cl.
 *B01D 29/05* (2006.01)
 *C12M 1/26* (2006.01)
 *G01N 1/22* (2006.01)

(52) U.S. Cl.
 CPC ............ *B01D 29/05* (2013.01); *C12M 33/14* (2013.01); *G01N 1/2205* (2013.01)

(58) Field of Classification Search
 CPC ........ B01D 29/05; B01D 29/03; B01D 35/30; B01D 46/10; C12M 33/14
 See application file for complete search history.

(56) References Cited

U.S. PATENT DOCUMENTS 6,183,645 B1 *   2/2001   DeWitt ................. B01D 11/04
                                                        210/634
2007/0261556 A1    11/2007   Kasai et al.

FOREIGN PATENT DOCUMENTS

| EP | 1923116 A1 | 5/2008 |
| JP | S58174203 U | 11/1983 |
| JP | 2006102575 A | 4/2006 |
| JP | 2011173054 A | 9/2011 |
| JP | 2013096394 A | 5/2013 |

OTHER PUBLICATIONS

International Search Report issued for PCT/JP2017/001590, dated Apr. 4, 2017.
Written Opinion of the International Searching Authority issued for PCT/JP2017/001590, dated Apr. 4, 2017.

* cited by examiner

*Primary Examiner* — Benjamin M Kurtz
(74) *Attorney, Agent, or Firm* — Arent Fox LLP

(57) ABSTRACT

A filtration filter device according to the present invention includes a filtration filter that filters out a filtration object contained in a fluid and a housing in which the filtration filter is disposed. The housing includes a fluid inlet passage that faces one main surface of the filtration filter and a fluid outlet passage that faces the other main surface of the filtration filter. An inner peripheral surface of at least one of the fluid inlet passage and the fluid outlet passage is undulated.

7 Claims, 3 Drawing Sheets

FILTRATION FILTER DEVICE

CROSS REFERENCE TO RELATED APPLICATIONS

The present application is a continuation of International application No. PCT/JP2017/001590, filed Jan. 18, 2017, which claims priority to Japanese Patent Application No. 2016-025954, filed Feb. 15, 2016, the entire contents of each of which are incorporated herein by reference.

BACKGROUND OF THE INVENTION

The present invention relates to a filtration filter device that filters out a filtration object contained in a fluid.

BACKGROUND ART

An example of filtration filter devices of this type is described in Japanese Unexamined Patent Application Publication No. 2011-173054. The filtration filter device described therein includes a filtration filter that filters out a filtration object contained in a fluid and a housing in which the filtration filter is disposed. The housing includes a fluid inlet passage that faces one main surface of the filtration filter and a fluid outlet passage that faces the other main surface of the filtration filter.

However, filtration filter devices still have room for improvement in efficiency in filtering out a filtration object. An object of the present invention, which addresses the above problem, is to provide a filtration filter device that can improve efficiency in filtering out a filtration object.

BRIEF DESCRIPTION OF THE INVENTION

In order to achieve the object, a filtration filter device according to an aspect of the present invention includes a filtration filter that filters out a filtration object contained in a fluid and a housing in which the filtration filter is disposed. The housing includes a fluid inlet passage that faces one main surface of the filtration filter and a fluid outlet passage that faces the other main surface of the filtration filter. An inner peripheral surface of at least one of the fluid inlet passage and the fluid outlet passage has undulation in a peripheral direction.

With the present invention, it is possible to provide a filtration filter device that can improve efficiency in filtering out a filtration object.

DESCRIPTION OF EMBODIMENTS

Figure 1:
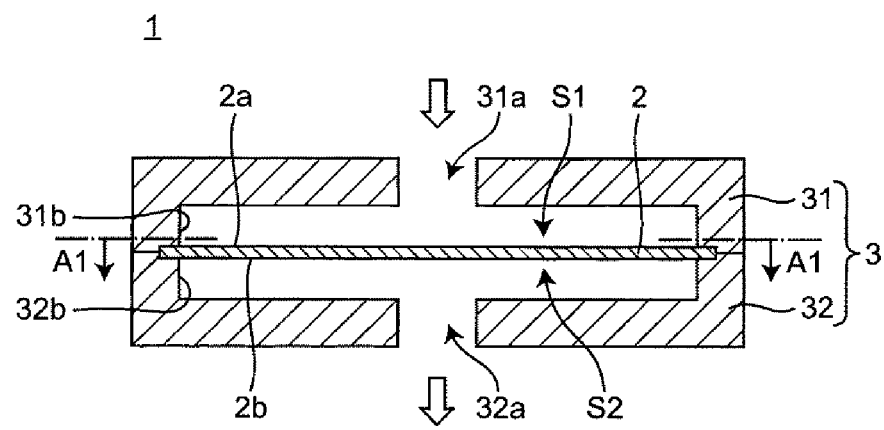
FIG. 1 is a schematic sectional view of a filtration filter device according to an embodiment of the present invention.

The inventors extensively investigated ways to improve efficiency in filtering out a filtration object and obtained the following findings.

Typically, when a fluid including a filtration object passes through a filtration filter, the filtration filter generates resistance and the speed of the fluid decreases as the fluid approaches the filtration filter. Therefore, the filtration object tends to accumulate in a region near the filtration filter.

The inventors found that, when filtration was performed by causing the fluid to pass through an existing filtration filter device from a fluid inlet passage of the filtration filter device, the filtration object adhered to an inner peripheral surface of the fluid inlet passage leading up to the filtration filter. As a result, the filtration object impeded flow of the fluid and filtration efficiency decreased. The inventors also found that substances that had passed through the filtration filter adhered to the inner peripheral surface of the fluid outlet passage and that these substances also impeded flow of the fluid and decreased the filtration efficiency. The inventors further found that the filtration object tended to accumulate in a central part the filtration filter itself and that this accumulation of the filtration object impeded flow of the fluid causing the filtration efficiency to be decreased.

The inventors intensively examined these new findings and found that it is possible to suppress adhesion of the filtration object to the inner peripheral surface of at least one of the fluid inlet passage and the fluid outlet passage by forming an undulation along at least part of the inner peripheral surface of the filter housing in the peripheral direction. The inventors also found the following: by forming the undulation, a fluid that has been bounced back by the filtration filter collides with the undulation causing the fluid to flow in diverse directions. As a result, eddy flow or turbulent flow is generated in the fluid inlet passage and/or the fluid outlet passage and accumulation of the filtration object in the central part of the filter can be suppressed.

The inventors have used these findings to design an improved filtration filter device in accordance with the present application.

A filtration filter device according to one aspect of the present invention includes a filtration filter that filters out a filtration object contained in a fluid; and a housing in which the filtration filter is disposed, the housing including a fluid inlet passage that faces one main surface of the filtration filter and a fluid outlet passage that faces the other main surface of the filtration filter. An inner peripheral surface of at least one of the fluid inlet passage and the fluid outlet passage has undulation in a peripheral direction.

With this structure, the inner peripheral surface of at least one of the fluid inlet passage and the fluid outlet passage is formed with an undulation in the peripheral direction. Therefore, it is possible to suppress adhesion of the filtration object to the inner peripheral surface and to suppress accumulation of the filtration object in a central part of the filtration filter. Accordingly, filtration efficiency can be improved.

Preferably, at least a portion that is in contact with the filtration filter has the undulation. With this structure, it is possible to more effectively suppress adhesion of the filtration object and to improve filtration efficiency.

Preferably, the undulation includes ridges and troughs that are alternately arranged, and the ridges and the troughs extend in a direction in which the fluid flows. With this structure, it is possible to reduce pressure loss due to the ridges and the troughs and to improve filtration efficiency.

Preferably, a pitch of the ridges and a pitch of the troughs are each smaller than an average particle size of the filtration object. With this structure, it is possible to suppress entry of the filtration object into the troughs and to reduce the contact area between the filtration object and the inner peripheral surface. As a result, it is possible to further suppress adhesion of the filtration object to the inner peripheral surface.

Preferably, a pitch of the ridges and a pitch of the troughs are each smaller than or equal to a pitch of through-holes that are formed in the filtration filter to filter out the filtration object. The width of each of the through-holes in the filtration filter is set smaller than the average particle size of the filtration object in order to filter out the filtration object. Accordingly, with this structure, it is possible to further reliably suppress entry of the filtration object into the troughs and to further suppress adhesion of the filtration object to the inner peripheral surface.

Preferably, the troughs are located at positions corresponding to through-holes that are formed in the filtration filter to filter out the filtration object. With this structure, compared with a case where the ridges are located at positions corresponding to the through-holes, it is possible to increase the opening area of the filtration filter and to improve filtration efficiency.

Preferably, at least one of the fluid inlet passage and the fluid outlet passage is divided into a plurality of flow passages, and an inner peripheral surface of at least one of the plurality of flow passages has undulation in a peripheral direction. With this structure, since the flow-path area of one flow passage is smaller than the flow-path area of the fluid inlet passage or the fluid outlet passage, the effect of the undulation can be increased. Thus, it is possible to suppress adhesion of the filtration object to the inner peripheral surface of the flow passage and to suppress accumulation of the filtration object in a central part of the filtration filter. Accordingly, filtration efficiency can be improved.

Hereafter, an embodiment of the present invention will be described with reference to the drawings.

Embodiment

The structure of a filtration filter device according to an embodiment will be described. FIG. 1 is a schematic sectional view of a filtration filter device according to an embodiment of the present invention.

As illustrated in FIG. 1, a filtration filter device 1 includes a filtration filter 2 and a housing 3 in which the filtration filter 2 is disposed.

The housing 3 includes a first housing portion 31 and a second housing portion 32. The first and second housing portions 31 and 32 hold an outer peripheral portion of the filtration filter 2 therebetween by, for example, being fitted together. The first housing portion 31 includes a fluid inlet passage 31a that faces one main surface 2a of the filtration filter 2. A portion S1 of the fluid inlet passage 31a facing the upper main surface 2a of the filtration filter 2 (i.e., the space above the main surface 2a of the filtration filter 2) is enlarged so that a fluid can be supplied to the entirety of the filtration filter 2 excluding the outer peripheral portion. The second housing portion 32 includes a fluid outlet passage 32a that faces the lower main surface 2b of the filtration filter 2. A portion S2 of the fluid outlet passage 32a facing the lower main surface 2b of the filtration filter 2 (i.e., the space below the one main surface 2b of the filtration filter 2) is enlarged so that a fluid that has passed through the filtration filter 2, excluding the outer peripheral portion, can be discharged.

In use, a fluid including a filtration object is supplied to the filtration filter 2 through the fluid inlet passage 31a and the filtration object is filtered out by the filtration filter 2. The fluid is discharged to the outside of the filtration filter device 1 through the fluid outlet passage 32a.

In the present embodiment, the filtration object is preferably a biological object contained in a liquid. In the present specification, the term "biological object" refers to an object derived from a living thing, such as a cell (eukaryote), a bacterium (eubacterium), a virus, or the like. Examples of a cell (eukaryote) include an ovum, a spermatozoon, an induced pluripotent stem cell (iPS cell), an ES cell, a stem cell, a mesenchymal stem cell, a mononuclear cell, a single cell, a cell cluster, a floating cell, an adhesive cell, a nerve cell, a leucocyte, a lymphocyte, a regenerative medicine cell, an autologous cell, a cancer cell, a circulating tumor cell (CTC), a HL-60, a HELA, and fungi. Examples of bacteria (eubacteria) include gram-positive bacteria, gram-negative bacteria, *Escherichia coli*, and a tubercle bacillus. Examples of a virus include a DNA virus, an RNA virus, a rotavirus, an (avian) influenza virus, a yellow fever virus, a dengue fever virus, an encephalitis virus, a hemorrhagic fever virus, and an immunodeficiency virus.

Figure 2:
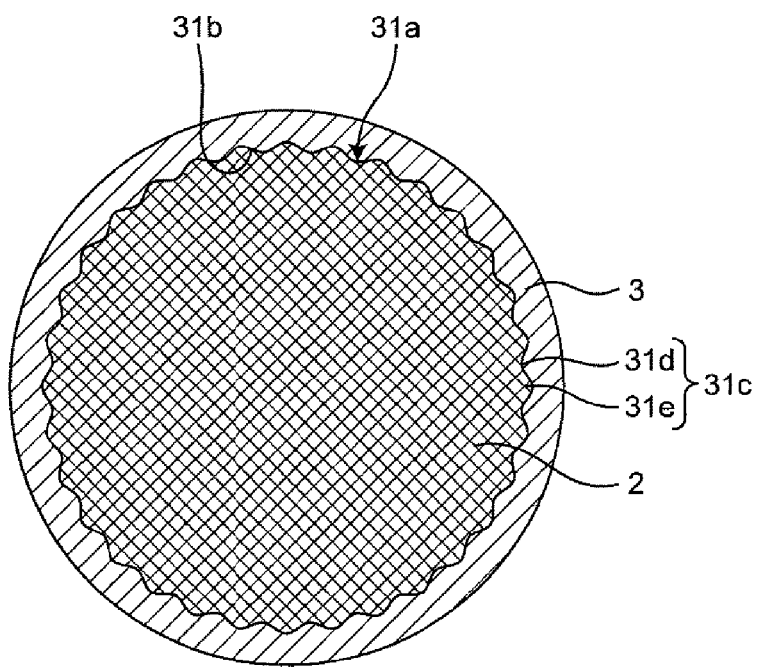
FIG. 2 is a sectional view taken along line A1-A1 of FIG. 1.

FIG. 2 is a sectional view taken along line A1-A1 of FIG. 1. As illustrated in FIG. 2, an inner peripheral surface 31b of the fluid inlet passage 31a has a (curtain-like) undulation 31c along its inner periphery. In the present embodiment, the undulation 31c has a smooth (sinusoidal) shape. The undulation 31c includes ridges 31d and troughs 31e that are alternately arranged and extend in a direction in which a fluid flows in order not to impede the flow of the fluid. In other words, the ridges 31d and the troughs 31e extend in a direction that intersects (for example, in a direction that is perpendicular to) the main surfaces 2a and 2b of the filtration filter 2.

Figure 3:
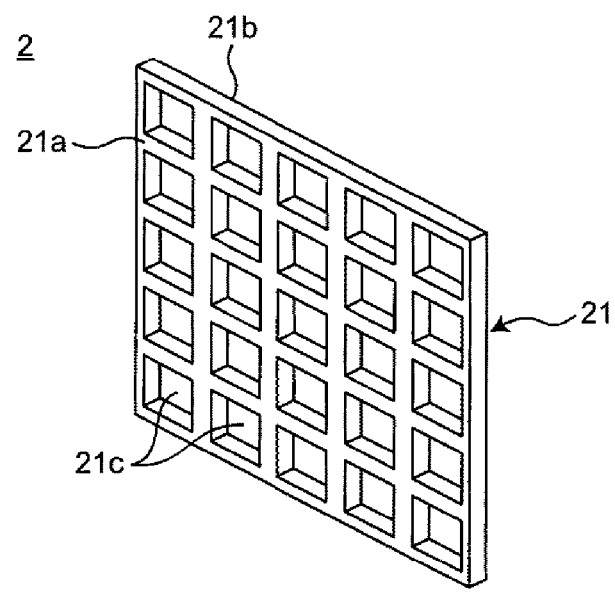
FIG. 3 is a schematic enlarged partial perspective view of a filtration filter.

FIG. 3 is a schematic enlarged perspective view of a portion (a square subsection) of the filtration filter 2. As illustrated in FIG. 3, the filtration filter 2 preferably includes a porous metal film 21 which at least partially filters out a filtration object contained in a fluid.

As illustrated in FIG. 3, the porous metal film 21 has a pair of main surfaces 21a and 21b that face (oppose) each other. The porous metal film 21 has a plurality of through-holes 21c that extend through the main surfaces 21a and 21b. The through-holes 21c serve to separate a biological object from a fluid. The shape and dimensions of each of the through-holes 21c are appropriately set in accordance with the shape and size of the biological object to be separated from the fluid. The through-holes 21c are arranged, for example, at a regular pitch or at a periodic pitch. The shape of each of the through-holes 21c is, for example, a square as viewed from the main surface 21a side of the porous metal film 21. In the present embodiment, the through-holes 21c are arranged in a square-grid pattern. The dimensions of each of the through-holes 21c are, for example, a length of 0.1 µm or greater and 500 µm or smaller and a width of 0.1 µm or greater and 500 µm or smaller. The pitch of the through-holes 21c is, for example, greater than the length of the sides of each of the through-holes 21c and smaller than or equal to ten times the length of the sides of the through-hole 21c, and, preferably, smaller than or equal to three times the length of the sides of the through-hole 21c. The opening ratio of the through-holes 21c in the porous metal film 21 is, for example, 10% or higher.

Examples of the material of the porous metal film 21 include gold, silver, copper, nickel, stainless steel, palladium, titanium, and an alloy of any of such metals. The dimensions of the porous metal film 21 are, for example, a diameter of 8 mm, and a thickness of 0.1 µm or greater and 100 µm or smaller. The outer shape of the porous metal film 21 is, for example, a circle, an ellipse, or a polygon. In the present embodiment, the outer shape of the porous metal film 21 is a circle. The through-holes 21c may be or may not be formed in an outer peripheral portion of the porous metal film 21.

Figure 4:
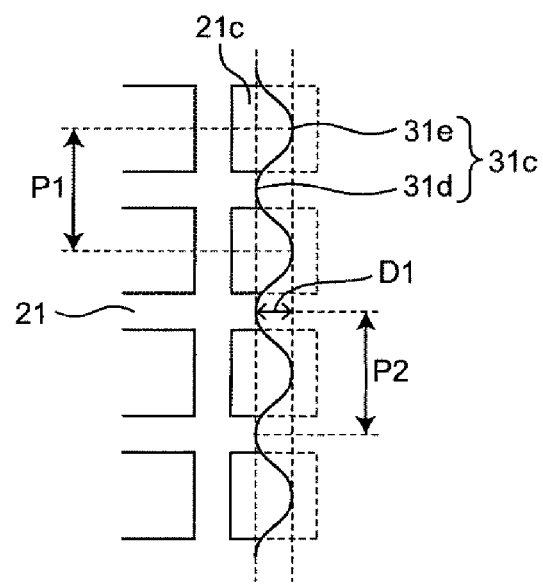
FIG. 4 is a partial enlarged plan view illustrating a contact portion where an inner peripheral surface of a fluid inlet passage is in contact with the filtration filter.

FIG. 4 is a partial enlarged plan view of the area where the inner peripheral surface 31b (FIG. 2) of the fluid inlet passage 31a is in contact with the filtration filter 2. In the present embodiment, the ridges 31d are located at positions that correspond to grids of the porous metal film 21 that define the through-holes 21c. The troughs 31e are located at positions corresponding to the location of the through-holes 21c (preferably the center of the through-holes 21c). In other words, the troughs 31e are located at positions that overlap the through-holes 21c in plan view. The ridges 31d and the troughs 31e are arranged at pitches P1 and P2, respectively, each of which is preferably substantially the same as the pitch of the through-holes 21c. The phrase "the pitch of the through-holes 21c" refers to, for example, the distance between the centroids of any adjacent through-holes 21c. In other words, the ridges 31d and the troughs 31e are arranged at substantially the same pitch as the through-holes 21c. The height (length) D1 of the undulation 31c as measured from the top of the ridge 31d to the bottom of the trough 31e is preferably smaller than the average particle size of a filtration object.

In the present embodiment, as with the inner peripheral surface 31b of the fluid inlet passage 31a, an inner peripheral surface 32b of the fluid outlet passage 32a illustrated in FIG. 1 is also formed with an undulation (not shown) in the peripheral direction. Description of this undulation, which is similar to the undulation 31c of the inner peripheral surface 31b of the fluid inlet passage 31a, will be omitted.

In the present embodiment, the inner peripheral surface 31b of the fluid inlet passage 31a has the undulation 31c in the peripheral direction (e.g., an undulation formed along the inner peripheral surface 31). With this structure, it is possible to suppress adhesion of a filtration object to the inner peripheral surface 31b of the fluid inlet passage 31a and to suppress accumulation of the filtration object in a central part of the filtration filter 2. Accordingly, filtration efficiency can be improved.

Moreover, in the present embodiment, the inner peripheral surface 32b of the fluid outlet passage 32b has undulation in the peripheral direction. With this structure, it is possible to suppress adhesion of substances that are contained in the fluid and that have passed through the filtration filter 2 to the inner peripheral surface 32b of the fluid outlet passage 32a.

At least a portion of the inner peripheral surface 31b of the fluid inlet passage 31a and a portion of the inner peripheral surface 32b of the fluid outlet passage 32a that are in contact with the filtration filter 2 (for example, portions near the filtration filter 2 to which a filtration object tends to adhere) may each have the undulation 31c. With this structure, it is possible to more effectively suppress adhesion of a filtration object.

In the present embodiment, the undulation 31c includes ridges 31d and the troughs 31e that are alternately arranged, and the ridges 31d and the troughs 31e extend in the direction in which the fluid flows. With this structure, it is possible to reduce pressure loss due to the ridges 31d and the troughs 31e and to improve filtration efficiency.

In the present embodiment, the ridges 31d and the troughs 31e are arranged at the pitches P1 and P2, respectively, each of which is substantially the same as the pitch of the through-holes 21c. The through-holes 21c, for filtering out a filtration object, are preferably each smaller than the average particle size of the filtration object. Therefore, by arranging the ridges 31d and the troughs 31e at the pitches P1 and P2, each of which is substantially the same as the pitch of the through-holes 21c, it is possible to suppress entry of the filtration object into the troughs 31e and to reduce the contact area between the filtration object and the inner peripheral surface 31b. As a result, it is possible to further suppress adhesion of the filtration object to the inner peripheral surface 31b of the fluid inlet passage 31a.

In the present embodiment, the troughs 31e are located at positions corresponding to the through-holes 21c of the filtration filter 2. With this structure, compared with a case where the ridges 31d are located at positions corresponding to the through-holes 21c, it is possible to increase the opening area of the filtration filter 2 and to improve filtration efficiency.

The pitches P1 and P2 of the ridges 31d and the troughs 31e each may be smaller than the average particle size of the filtration object. In this case, it is possible to suppress entry of the filtration object into the troughs 31e and to further suppress adhesion of the filtration object to the inner peripheral surface 31b. Preferably, the pitches P1 and P2 of the ridges 31d and the troughs 31e are each smaller than or equal to the pitch of the through-holes 21c. Thus, it is possible to further suppress adhesion of the filtration object to the inner peripheral surface 31b.

The present invention is not limited to the above embodiment and may be modified in various ways. For example, in the above embodiment, a filtration object is a biological object contained in a liquid. However, this is not required. The filtration object may be a substance contained in a gas. In other words, the filtration object may be any substance contained in a fluid, and may be, for example, airborne PM 2.5.

In the above embodiment, the porous metal film 21 is used to filter out a biological object from a liquid. However, the invention is not so limited. For example, the porous metal film 21 may be used to concentrate a liquid.

In the above embodiment, the portions S1 and S2 of the fluid inlet passage 31a and the fluid outlet passage 32a, which respectively face the main surfaces 2a and 2b of the filtration filter 2, are enlarged. However, the invention is not so limited. For example, the fluid inlet passage 31a and the fluid outlet passage 32a may be flow passages each having a uniform flow-path area.

In the above embodiment, the inner peripheral surfaces 31b and 32b of the fluid inlet passage 31a and the fluid outlet passage 32a both have undulations. However, the invention is not so limited. Only one of the inner peripheral surfaces 31b and 32b of the fluid inlet passage 31a and the fluid outlet passage 32a may have undulation. The pitches P1 and P2 of the ridges 31d and the troughs 31e on the fluid inlet passage 31a side may be the same as or may differ from those on the fluid outlet passage 32a side. The pitches P1 and P2 of the ridges 22d and the troughs 22e need not be constant in the peripheral direction. The pitches of the ridges 22d and the troughs 22e may vary in the direction in which the fluid flows.

Figure 5:
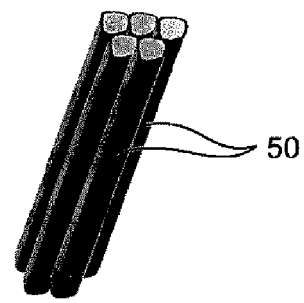
FIG. 5 is a perspective view of a modification of a fluid inlet passage or a fluid outlet passage.

In the above embodiment, the fluid inlet passage 31a and the fluid outlet passage 32a are each an annular flow passage. However, the invention is not so limited. At least one of the fluid inlet passage 31a and the fluid outlet passage 32a may be divided into a plurality of flow passages. For example, at least one of the fluid inlet passage 31a and the fluid outlet passage 32a may be composed of a plurality of annular members 50 as illustrated in FIG. 5. In this case, an inner peripheral surface of at least one of the plurality of annular members 50 may have undulation in the peripheral direction. With this structure, since the flow-path area of one annular member 50 is smaller than the flow-path area of the fluid inlet passage 31a or the fluid outlet passage 32a, the effect of the undulation can be increased. Thus, it is possible to suppress adhesion of a filtration object to the inner peripheral surface of the annular member 50 and to suppress accumulation of a filtration object in a central part of the filtration filter 2. Accordingly, filtration efficiency can be improved.

Example

Next, a filtration filter according to an Example will be described.

First, as illustrated in FIG. 1, a filtration filter device according to the Example was made by fitting the first housing portion 31 and the second housing portion 32 together so as to hold an outer peripheral portion of the filtration filter 2 therebetween.

The first housing portion 31 and the second housing portion 32 were each made by machining polyacetal. The outer shape of the first housing portion 31 and the second housing portion 32 as viewed in the direction of flow of a fluid was circular. The diameter of the inlet opening of the fluid inlet passage 31a was 2 mm, and the diameter of the portion S1 of the fluid inlet passage 31a facing the main surface 2a of the filtration filter 2 was 6 mm. The diameter of the portion S2 of the fluid outlet passage 32a facing the main surface 2b of the filtration filter 2 was 6 mm, and the diameter of the outlet opening of the fluid outlet passage 32a was 2 mm. The length from the inlet opening of the fluid inlet passage 31a to the outlet opening of the fluid outlet passage 32a was 6 mm. The total length of the portion S1 and the portion S2 in the direction of the flow of the fluid was about 4 mm. The undulation 31c of the fluid inlet passage 31a and the undulation of the fluid outlet passage 32a were formed by machining so as to have a smooth (sinusoidal) shape. The difference in height between the ridges 31d and the troughs 31e was 100 µm. The pitches P1 and P2 of the ridges 31d and the troughs 31e were 100 µm.

The filtration filter 2 was disposed so that the main surface 2a was perpendicular to the direction of the flow of the fluid. The porous metal film 21 of the filtration filter 2 was a porous film made of nickel and having a thickness of 1.0 µm. The outer shape of the porous metal film 21 was a circle having a diameter of 7.8 mm. The plurality of through-holes 21c were formed in a square-grid pattern in a region centered on the center of the porous metal film 21 and having a diameter of 6 mm. The outer shape of each of the through-holes 21c was a square of side 1.9 µm. The pitch (grid pitch) of the through-holes 21c was 2.6 µm.

Using the filtration filter device according to the Example, a phosphate buffered saline (PBS) solution of 1 ml containing $1 \times 10^5$ HI-60 cells was filtered, and a part of the solution that passed through the filtration filter 2 (hereinafter, referred to as "filtrate") was collected. The cells HL-60 had substantially spherical shapes and an average particle size of about 11 µm. Filtration was performed by using a dead-end filtration method utilizing the own weight of the PBS solution. It took about 20 minutes to filter the PBS solution.

Subsequently, a PBS solution of 1 ml was poured into the filtration filter device according to the Example from the opposite direction, and a part of the solution that passed through the filtration filter 2 (hereinafter, referred to as "recovered liquid") was collected.

Subsequently, the amounts of the filtrate and the recovered liquid that have passed through the filtration filter 2 and the numbers of cells contained in the filtrate and the recovered liquid were measured.

As a result, the amount of the filtrate was 0.8 ml, and the number of cells contained in the filtrate was $5 \times 10^2$ or less. The amount of the recovered liquid was 1.2 ml, and the number of cells contained in the recovered liquid was $0.93 \times 10^5$. Thus, it was confirmed that, compared with the PBS solution before being filtered, the concentration ratio was 0.83 and the cell recovery ratio was 73%.

Subsequently, the filtration filter device according to the Example was disassembled and the filtration filter 2, the inner peripheral surface 31b of the fluid inlet passage 31a, and the inner peripheral surface 32b of the fluid outlet passage 32a were observed by using a microscope.

It was observed that cells were trapped in the plurality of through-holes 21c of the filtration filter 2. It was not observed that cells adhered to the inner peripheral surface 31b of the fluid inlet passage 31a and the inner peripheral surface 32b of the fluid outlet passage 32a.

Comparative Example

Figure 6:
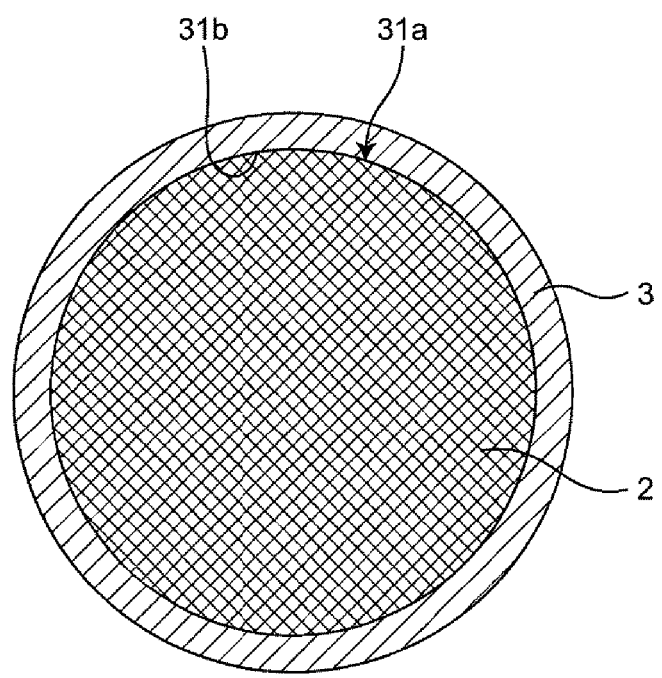
FIG. 6 is a schematic sectional view of a filtration filter device according to a comparative example.

A filtration filter device according to a Comparative Example, which had the same structure as the filtration filter device 1 according to Example except that the inner peripheral surface 31b of the fluid inlet passage 31a and the inner peripheral surface 32b of the fluid outlet passage 32a were uniform (i.e., did not have undulations), was made. FIG. 6 is a schematic sectional view of the filtration filter device according to Comparative Example.

By using the filtration filter device according to Comparative Example, a phosphate buffered saline (PBS) solution of 1 ml containing $1 \times 10^5$ HI-60 cells was filtered under the same conditions as those of Example. It took about 45 minutes to filter the PBS solution.

As a result, the amount of the filtrate was 0.5 ml, and the number of cells contained in the filtrate was $5 \times 10^2$ or smaller. The amount of the recovered liquid was 1.5 ml, and the number of cells contained in the recovered liquid was $0.27 \times 10^5$. Thus, it was confirmed that, compared with the PBS solution before being filtered, the concentration ratio was 0.67 and the cell recovery ratio was 17%.

Subsequently, the filtration filter device according to Comparative Example was disassembled; and the filtration filter 2, the inner peripheral surface 31b of the fluid inlet passage 31a, and the inner peripheral surface 32b of the fluid outlet passage 32a were observed by using a microscope.

As a result, it was observed that cells were trapped in the plurality of through-holes 21c of the filtration filter 2. It was observed that a large number of cells adhered to the inner peripheral surface 31b of the fluid inlet passage 31a and the inner peripheral surface 32b of the fluid outlet passage 32a.

CONCLUSION

Thus, it was confirmed that the filtration filter device according to Example has an effect of preventing adhesion of a filtration object.

The present invention is not limited to the embodiment described above in detail with reference to the drawings. It is clear for persons skilled in the art that the embodiment can be modified or adjusted in various ways. It is to be understood such modifications and adjustments are within the scope of the present invention described in the claims.

The present invention, which can improve efficiency in filtering out a filtration object, is applicable to a filtration filter device that filters out a filtration object, such as a biological object or PM 2.5, contained in a fluid.

REFERENCE SIGNS LIST 1 filtration filter device
2 filtration filter
2a, 2b main surface
3 housing
21 porous metal film
21a, 21b main surface
21c through-hole
31 first housing portion
31a fluid inlet passage
31b inner peripheral surface
31c undulation
31d ridge
31e trough
32 second housing portion
32a fluid outlet passage
32b inner peripheral surface
50 annular member

The invention claimed is:

1. A filtration filter device comprising:
a filtration filter for filtering out a filtration object contained in a fluid, the filtration filter having opposed first and second main surfaces; and
a housing in which the filtration filter is disposed, the housing including a fluid inlet passage that faces the first main surface of the filtration filter and a fluid outlet passage that faces the second main surface of the filtration filter, an inner peripheral surface of at least one of the fluid inlet passage and the fluid outlet passage being undulated,
wherein at least a portion of the undulated inner peripheral surface or surfaces is in contact with the filtration filter, and
wherein the filtration filter is planar and extends along a plane, the undulated inner peripheral surface or surfaces including ridges and troughs that are alternately arranged and extend in a direction perpendicular to the plane of the filtration filter.

2. The filtration filter device according to claim 1, wherein a pitch of the ridges and a pitch of the troughs are each smaller than or equal to a pitch of through-holes that are formed in the filtration filter.

3. The filtration filter device according to claim 1, wherein the troughs are located at positions corresponding to through-holes that are formed in the filtration filter.

4. The filtration filter device according to claim 3, wherein the center of each trough is located at the center of a respective through-hole.

5. The filtration filter device according to claim 1, wherein:
at least one of the fluid inlet passage and the fluid outlet passage is divided into a plurality of flow passages, and
an inner peripheral surface of at least one of the plurality of flow passages is undulated.

6. The filtration filter device according to claim 1, wherein only a portion of the inner peripheral surface of at least one of the fluid inlet and fluid outlet passages is undulated.

7. The filtration filter device according to claim 1, wherein the undulation is sinusoidal.

* * * * *